(12) United States Patent
Lin et al.

(10) Patent No.: US 10,515,725 B2
(45) Date of Patent: Dec. 24, 2019

(54) HEALTH ASSESSMENT METHOD AND HEALTH ASSESSMENT DEVICE FOR WORKPIECE PROCESSING APPARATUS

(71) Applicant: Industrial Technology Research Institute, Chu-Tung, Hsinchu (TW)

(72) Inventors: Chung-Wei Lin, Zhubei (TW); Te-Ming Chen, Taipei (TW); Chuang-Hua Chueh, Taipei (TW); Sen-Chia Chang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 816 days.

(21) Appl. No.: 14/983,191

(22) Filed: Dec. 29, 2015

(65) Prior Publication Data

US 2017/0132387 A1 May 11, 2017

(30) Foreign Application Priority Data

Nov. 6, 2015 (TW) .............................. 104136681 A

(51) Int. Cl.
*G16H 50/30* (2018.01)
*G16H 40/63* (2018.01)

(52) U.S. Cl.
CPC .............. *G16H 50/30* (2018.01); *G16H 40/63* (2018.01)

(58) Field of Classification Search
CPC ......... G06F 19/00; G16H 40/63; G16H 50/30
USPC ....................................................... 703/6–7
See application file for complete search history.

(56) References Cited

U.S. PATENT DOCUMENTS

| | | | |
|---|---|---|---|
| 6,810,360 B2 | 10/2004 | Fujishima et al. | |
| 8,295,966 B2 | 10/2012 | Choi et al. | |
| 8,774,956 B2 | 7/2014 | Moyne et al. | |
| 2003/0014387 A1* | 1/2003 | Kreidler | G05B 19/4183 |
| 2003/0065481 A1 | 4/2003 | Fujishima et al. | |
| 2007/0100487 A1 | 5/2007 | Cheng et al. | |

(Continued)

FOREIGN PATENT DOCUMENTS

| | | |
|---|---|---|
| CN | 101598754 A | 12/2009 |
| CN | 101738991 A | 6/2010 |
| CN | 101804580 A | 8/2010 |

(Continued)

OTHER PUBLICATIONS

Tianyi Wang et al., "A similarity-based prognostics approach for Remaining Useful Life estimation of engineered systems", 2008 International Conference on Prognostics and Health Management, pp. 1-6.

(Continued)

*Primary Examiner* — Saif A Alhija
(74) *Attorney, Agent, or Firm* — Muncy, Geissler, Olds & Lowe, P.C.

(57) ABSTRACT

A health assessment method and a health assessment device of a workpiece processing apparatus are disclosed. The health assessment method includes the following steps. Acquire a first sensing data related to the workpiece processing apparatus at an operation stage of the workpiece processing apparatus. Set the first sensing data as a substitution of a first transform model to acquire a virtual workpiece quality. Set the virtual workpiece quality as a substitution of a second transform model to acquire a first virtual apparatus health index.

13 Claims, 5 Drawing Sheets

(56) References Cited

U.S. PATENT DOCUMENTS

2014/0195184 A1    7/2014   Maeda et al.
2014/0336791 A1   11/2014   Asenjo et al.

FOREIGN PATENT DOCUMENTS

| | | |
|---|---|---|
| CN | 102254788 A | 11/2011 |
| CN | 102521454 A | 6/2012 |
| CN | 103206932 A | 7/2013 |
| CN | 104657526 A | 5/2015 |
| JP | 2013-215809 A | 10/2013 |
| TW | 201020806 A | 6/2010 |
| TW | I4633348 B | 12/2014 |

OTHER PUBLICATIONS

Office Action dated Jun. 19, 2019 in application No. CN 201510917089.2.

\* cited by examiner

HEALTH ASSESSMENT METHOD AND HEALTH ASSESSMENT DEVICE FOR WORKPIECE PROCESSING APPARATUS

CROSS-REFERENCE TO RELATED APPLICATIONS

This non-provisional application claims priority under 35 U.S.C. § 119(a) on Patent Application No(s). 104US13348 filed in Taiwan, R.O.C. on Nov. 6, 2015, the entire contents of which are hereby incorporated by reference.

TECHNICAL FIELD

The disclosure relates to a health assessment method and a health assessment apparatus for a workpiece processing apparatus.

BACKGROUND

In the art, it is not easy to obtain a health index of a workpiece processing apparatus. In one aspect, only if the workpiece processing apparatus stops machining in an off-line mode (e.g. when the cutting tool is taken apart and then is subject to precision measurement) may its apparatus health index (e.g. the wear of the cutting tool) be obtained. At an operation mode under which a workpiece is being machined, a health index of the workpiece processing apparatus may not be obtained immediately.

In another aspect, it is not easy to obtain the ground truth related to an apparatus health index, too. A less data quantity of ground truths may cause that a great error occurs to a relevant model for estimating an apparatus health index. For example, an experiment result indicates that a relevant transform model of apparatus health indexes, which is established when the data quantity of ground truths is N/2, may have about 55% more errors than another relevant transform model, which is established when the data quantity of ground truths is N.

SUMMARY

According to one or more embodiments, the disclosure provides a health assessment method applied to a health assessment apparatus to assess a health state of a workpiece processing apparatus used to machine at least one workpiece. The health assessment method includes the following steps. At an operation stage of the workpiece processing apparatus, acquire first detection data related to the workpiece processing apparatus. Set the first detection data as a substitution of a first transform model to obtain a virtual workpiece quality. Set the virtual workpiece quality as a substitution of a second transform model to obtain a first virtual apparatus health index.

According to one or more embodiments, the disclosure provides a health assessment apparatus applied to a workpiece processing apparatus for machining at least one workpiece. The health assessment apparatus includes a detection data acquiring module, a first transform module, a second transform module, and a third transform module. The first transform module is coupled to the detection data acquiring module; the second transform module is coupled to the first transform module; the updating determination module is coupled to the first transform module, the second transform module and the third transform module. The detection data acquiring module acquires first detection data related to the workpiece processing apparatus at an operation stage of the workpiece processing apparatus. The first transform module sets the first detection data as a substitution of a first transform model to obtain a virtual workpiece quality. The second transform module sets the virtual workpiece quality as a substitution of a second transform model to obtain a first virtual apparatus health index. The third transform module sets the first detection data as a substitution of a third transform model to obtain a second virtual apparatus health index. The updating determination module compares the first virtual apparatus health index with the second virtual apparatus health index to determine whether to update the first transform model. When it is determined to update the first transform model, the updating determination module commands the first transform module to update the first transform model according to the third detection data and a plurality of relative third actual workpiece qualities. The third detection data is related to the workpiece processing apparatus.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
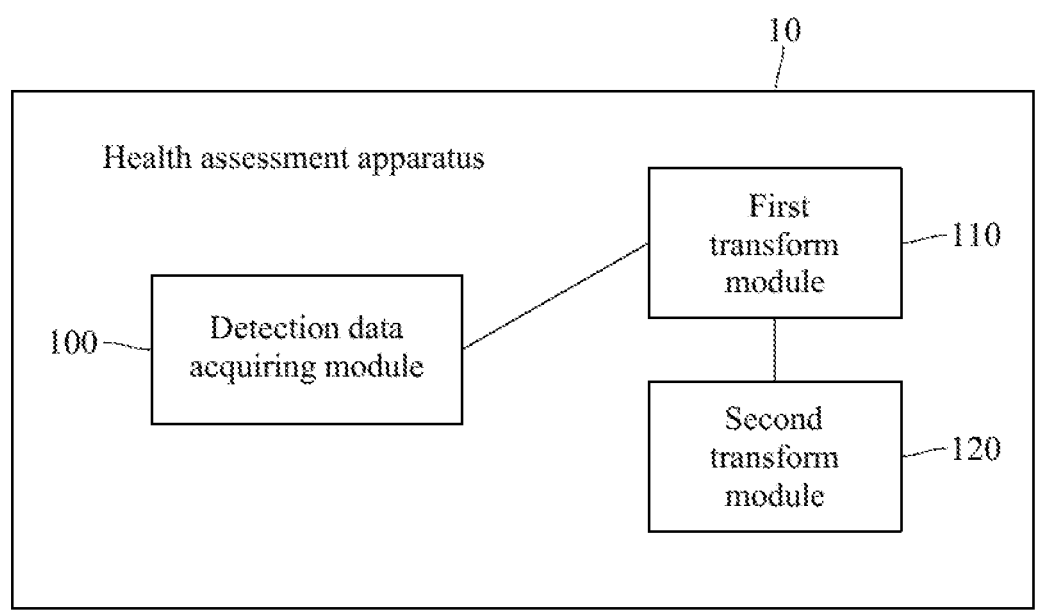
FIG. 1 is a block diagram of a health assessment apparatus for a workpiece processing apparatus in an embodiment.

FIG. 1 is a block diagram of a health assessment apparatus 10 for a workpiece processing apparatus in an embodiment. The health assessment apparatus 10 includes a detection data acquiring module 100, a first transform module 110, and a second transform module 120. The first transform module 110 is coupled to the detection data acquiring module 100, and the second transform module 120 is coupled to the first transform module 110. The health assessment apparatus 10 is applied to a workpiece processing apparatus used for machining at least one workpiece. For example, the workpiece processing apparatus is a cutting tool, which is used to cut the outer ring of a certain bearing workpiece.

In the disclosure, the detection data acquiring module 100 is, for example, a variety of detectors for capturing a variety of information about machining process. For example, the information about machining process includes information about vibration signals, high-frequency audio signals, and/or strain data, which are produced during the feeding and retracting of a workpiece processing apparatus and the machining process. The disclosure will not have any limitation in the sensor type and the acquired data. The first transform module 110 and the second transform module 120 are carried out by, for example, but not limited to, a variety of chips or microprocessors.

Figure 2:
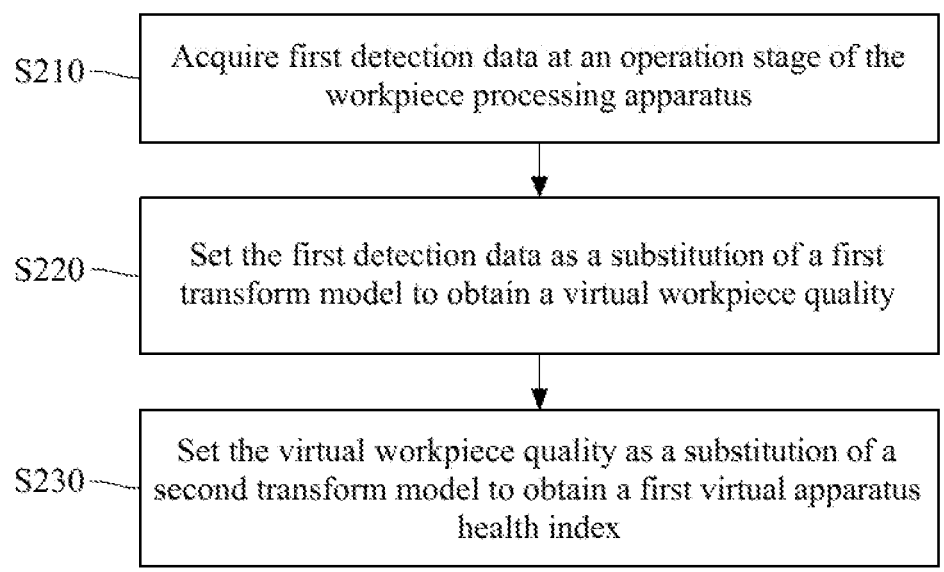
FIG. 2 is a flow chart of a health assessment apparatus for a workpiece processing apparatus in an embodiment.

FIG. 2 is a flow chart of a health assessment apparatus for a workpiece processing apparatus in an embodiment. The health assessment method includes steps S210~S230, as described below with respect to FIGS. 1 and 2. In step S210, the detection data acquiring module 100 at an operation stage of the workpiece processing apparatus acquires first detection data related to the workpiece processing apparatus. In step S220, the first transform module 110 sets the first detection data as a substitution of the first transform model to obtain a virtual workpiece quality.

In this embodiment, the first transform model is established according to second detection data and a plurality of relative first actual workpiece qualities. The second detection data herein is acquired by the detection data acquiring module 100 at a previous operation stage of the workpiece processing apparatus so the second detection data is acquired earlier than the first detection data. The first actual workpiece quality is a quality index obtained by measuring machined workpieces with a dimensional accuracy meter, or by referring to maintain record tables of workpieces. For example, the first actual workpiece quality is the inner diameter, seal groove diameter, seal mouth diameter or seal groove depth of an outer ring or the like of a certain bearing workpiece. The first transform model is a transform model established by the second detection data as an independent variable and the first actual workpiece qualities as dependent variables. Therefore, the first transform model is a transform formula related to detection data and the workpiece quality.

Since the first transform model is established according to the second detection data and the relative first actual workpiece qualities, a "virtual" workpiece quality, obtained by setting the first detection data as a substitution of the first transform model, represents an estimation value of this workpiece quality.

Note that the actual workpiece qualities requires an additional accurate measurement performed after the machining process finishes, so the measurement of actual workpiece qualities takes a relatively long time. In contrast with the measurement of actual workpiece qualities, the measurement of the above virtual workpiece quality only takes a relatively short time because it is obtained by setting the first detection data as a substitution of the first transform model.

In step S230, the second transform module 120 sets the virtual workpiece quality as a substitution of a second transform model to obtain a first virtual apparatus health index. In this embodiment, the second transform model is established according to a plurality of second actual workpiece qualities and a relative actual apparatus health index.

These second actual workpiece qualities come from the same source as the above first actual workpiece qualities. The second actual workpiece quality and the first actual workpiece quality are the same in an embodiment and are different in another embodiment. The actual apparatus health index herein is the actual wear of the cutting tool of the workpiece processing apparatus, which is measured by an electron microscopy. Other embodiments may be contemplated in which the actual apparatus health index is obtained in a different way. Note that the actual apparatus health index is usually obtained at an off-line stage when the workpiece processing apparatus stops machining. That is, the second transform model is established under the off-line stage. Other embodiments may be contemplated in which the second transform model is established by a different way at a certain operation stage where the workpiece processing apparatus is machining workpieces.

In an embodiment, the establishment of the second transform model using the second actual workpiece qualities and the relative actual apparatus health index may be carried out by a piecewise regression model. For example, a curve presenting a correlation between the second actual workpiece quality and a relative actual apparatus health index may be segmented by more turning points in an acceptable tolerance range in order to reduce the quantity of error occurring to the entire estimation of the second transform model.

In an embodiment, the second transform model is a transform model established using the second actual workpiece qualities as independent variables and using the actual apparatus health index as a dependent variable. Therefore, the second transform model is a transform formula related to the workpiece quality and the health degree of the apparatus.

Since the second transform model is established according to the second actual workpiece qualities and the relative actual apparatus health index, a "virtual" apparatus health index, obtained by setting the virtual workpiece quality as a substitution of the second transform model, is an estimation value of the health status of the apparatus.

In the aforementioned embodiment as described above, after the first detection data is acquired at the operation stage, the first virtual apparatus health index of the workpiece processing apparatus may rapidly be obtained using the first and second transform models established in advance.

Figure 3:
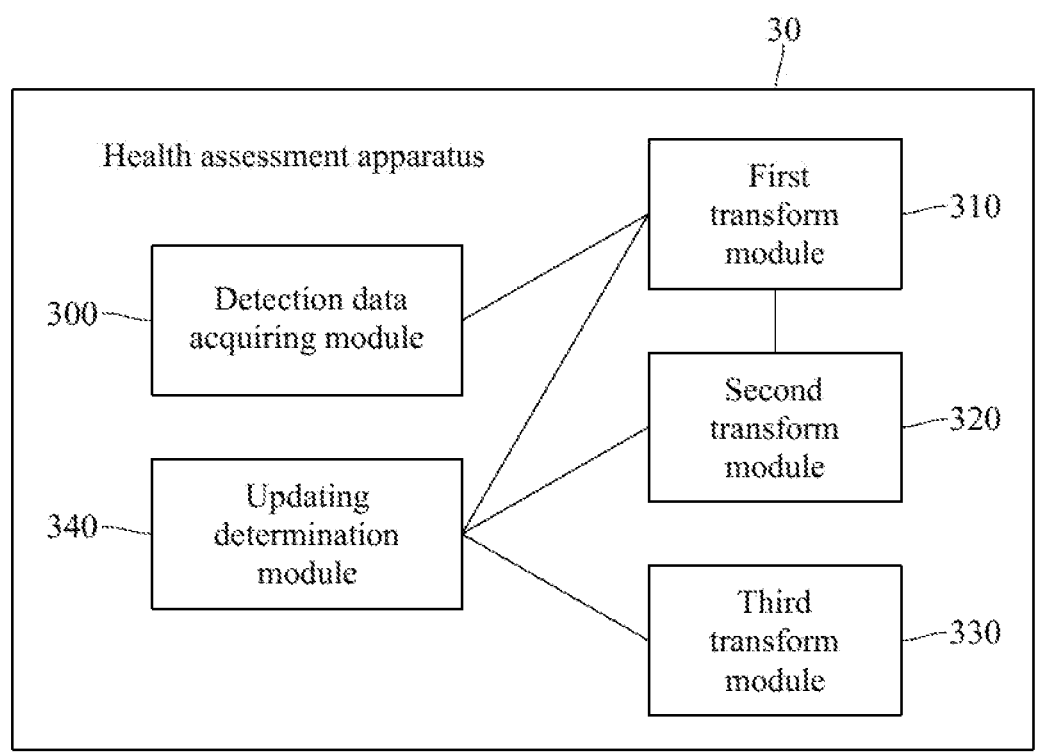
FIG. 3 is a block diagram of a health assessment apparatus for a workpiece processing apparatus in another embodiment.

FIG. 3 is a block diagram of a health assessment apparatus 30 for a workpiece processing apparatus in another embodiment. The health assessment apparatus 30 is applied to a workpiece processing apparatus for machining at least one workpiece. The health assessment apparatus 30 includes a detection data acquiring module 300, a first transform module 310, a second transform module 320, a third transform module 330, and an updating determination module 340. The first transform module 310 is coupled to the detection data acquiring module 300, the second transform module 320 is coupled to the first transform module 310, and the updating determination module 340 is coupled to the first transform module 310, the second transform module 320 and the third transform module 330.

The detection data acquiring module 300 is, for example, but not limited to, a variety of sensors for sensing a variety of information about the machining process. The first transform module 310, the second transform module 320, the third transform module 330 and the updating determination module 340 are embodied by, for example, but not limited to, various chips or microprocessors.

Figure 4:
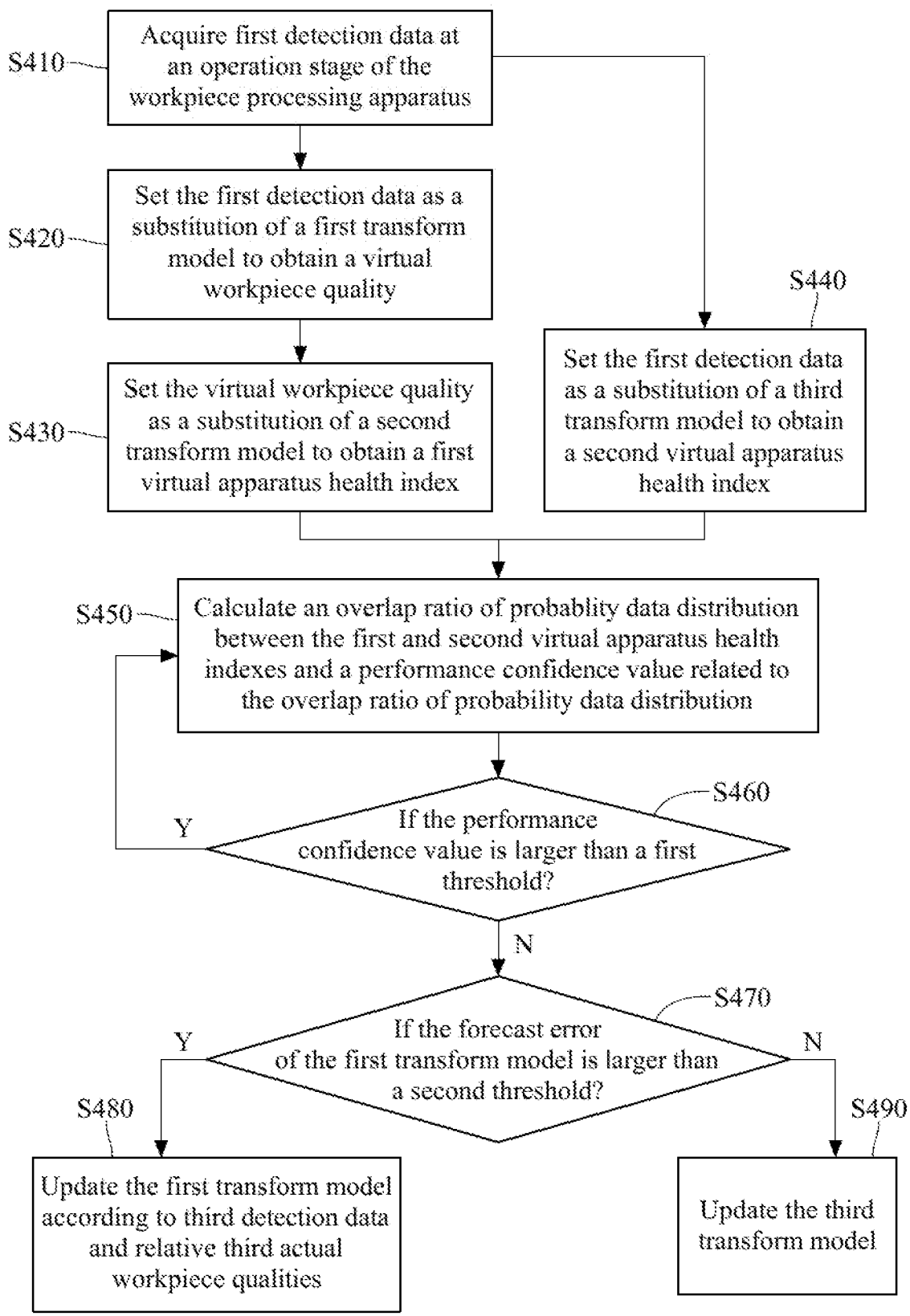
FIG. 4 is a flow chart of a health assessment apparatus for a workpiece processing apparatus in another embodiment.

FIG. 4 is a flow chart of a health assessment apparatus for a workpiece processing apparatus in another embodiment. The health assessment method includes steps S410~S490, as described below with respect to FIGS. 3 and 4. In step S410, the detection data acquiring module 300 acquires first detection data as the same as what the detection data acquiring module 100 does. In step S420, the first transform module 310 acquires a virtual workpiece quality as the same as what the first transform module 110 does.

In step S430, the second transform module 320 acquires first virtual apparatus health indexes as the same as what the second transform module 120 does. More functions of the first transform module 310 and the second transform module 320 will be described in detail later.

In step S440, the third transform module 330 sets the first detection data as a substitution of a third transform model to obtain a second virtual apparatus health index. For example, the third transform module 330 obtains the second virtual apparatus health index by a condition-based maintenance (CBM) technology or other relevant technologies. That is, the third transform model is a transform formula related to detection data and the health degree of apparatus.

The updating determination module 340 compares the first virtual apparatus health index with the second virtual apparatus health index to determine whether to update the first transform model; and when it is determined to update the first transform model, the updating determination module 340 commands the first transform module 310 to update the first transform model according to third detection data and a plurality of relative third actual workpiece qualities. This is described in detail in the following steps S450~S490.

In step S450, the updating determination module 340 further calculates an overlap ratio of probability data distribution between the first virtual apparatus health index and the second virtual apparatus health index of probability data distribution with a performance confidence value. In step S460, the updating determination module 340 determines whether the performance confidence value is larger than a first threshold. For example, the first and second virtual apparatus health indexes are two respective data distributions. If the overlap ratio of probability data distribution between the two data distributions in a statistical chart is relatively high, it indicates that the forecasting result of steps S410~S430 performed by the first transform module 310 and the second transform module 320 is similar to the forecasting result of steps S410~S440 performed by the third transform module 330. Accordingly, a relatively large performance confidence value (e.g. which is larger than the first threshold) may be obtained. If the overlap ratio of probability data distribution between the two data distributions have in the statistical chart is relatively low, it indicates that errors may occur to either steps S410~S430 or steps S410~S440, and that something needs to be updated or calibrated. Accordingly, a relatively small performance confidence value (e.g. which is not larger than the first threshold) may be obtained. When the updating determination module 340 determines that the performance confidence value is larger than the first threshold, the process may return to step S450.

In step S470, when determining that the performance confidence value is not larger than the first threshold, the updating determination module 340 further determines whether a forecast error of the first transform model is larger than a second threshold. As described above, if the forecasting result of steps S410~S430 is quite different from the forecasting result of steps S410~S440 (i.e. the performance confidence value is not larger than the first threshold), the updating determination module 340 first determines whether the forecast error of the first transform model is still within an acceptable range. Note that although the performing of steps S410~S430 is also involved with the first transform module 310 and the second transform module 320, errors may difficultly occur to the second transform model, and only the first transform model needs to be calibrated or updated.

In step S480, when determining that the forecast error of the first transform model is larger than a second threshold, the updating determination module 340 commands the first transform module 310 to update the first transform model according to the third detection data and the relative third actual workpiece qualities. When determining that the forecast error of the first transform model is not within the acceptable range, the updating determination module 340 needs to update the first transform model again. Moreover, a database may have a relatively great deal of third detection data as compared to the quantity of second detection data because the workpiece processing apparatus may have operated for a period of time; and the database may also have a relatively great deal of third actual workpiece qualities as compared to the quantity of first actual workpiece qualities because more machined workpieces may have been measured. Therefore, the first transform module 310 uses the information stored in the database to update the first transform model after receiving the updating command from the updating determination module 340.

In step S490, when determining that the forecast error of the first transform model is not larger than the second threshold, the updating determination module 340 commands the third transform module 330 to update the third transform model. Similarly, if the process of steps S410~S440 needs to be calibrated or updated, it may be performed to update the third transform model. The updating of the third transform model may be carried out by various ways and thus, will not be repeated hereinafter.

Figure 5:
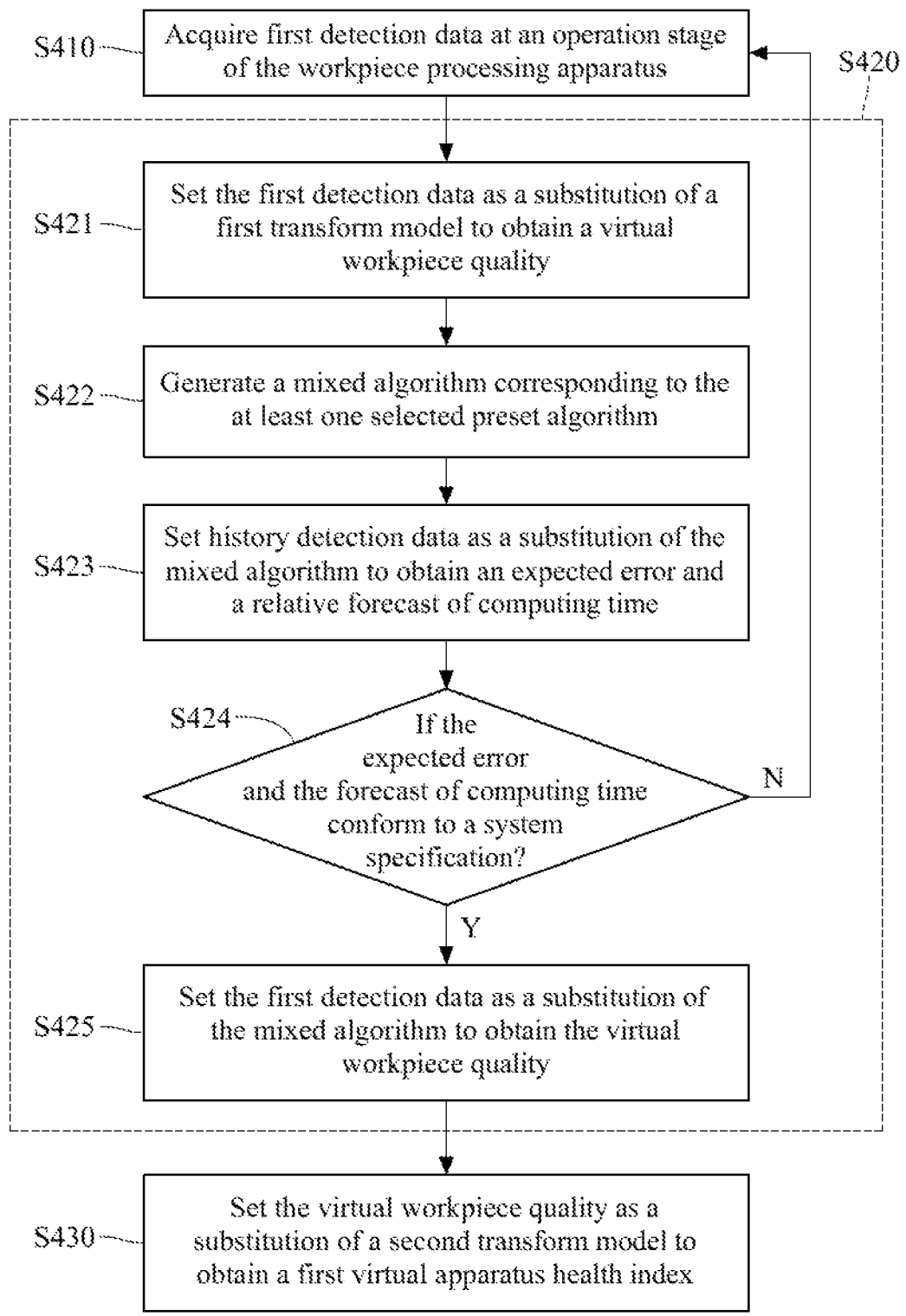
FIG. 5 is a flow chart of a health assessment apparatus for a workpiece processing apparatus in another embodiment.

FIG. 5 is a flow chart of a health assessment apparatus for a workpiece processing apparatus in another embodiment. In this embodiment, step S420 performed by the first transform module 310 includes steps S421~S425 for the generating of a modified first transform model. This is described in detail below.

In step S421, the first transform module 310 receives a selection command from an operation interface to select at least one of preset algorithms. In step S422, the first transform module 310 generates a mixed algorithm related to the first transform model according to the at least one selected preset algorithm. In step S423, the first transform module 310 sets history detection data as a substitution of the mixed algorithm to obtain an expected error and a forecast of computing time both related to the mixed algorithm, and displays the expected error and the forecast of computing time. Note that the first transform module 310 forecasts such information using the history detection data so that this step may be performed at the off-line stage of the workpiece processing apparatus in an embodiment. In step S424, the first transform module 310 determines whether the expected error and the forecast of computing time meet a system specification. When the first transform module 310 determines that the expected error and the forecast of computing time do not meet in the system specification, the method returns to step S421 in order to receive a selection command again.

Other embodiments may be contemplated in which the first transform module 310 sets the history detection data as substitutions of all the preset algorithms in order to display the expected error and the forecast of computing time of each preset algorithm. Therefore, a user may use such information as a reference when the user attempts to initially give a selection command or to resent a selection command.

In step S425, when determining that the expected error and the forecast of computing time meets the system specification, the first transform module 310 sets the first detection data as a substitution of the mixed algorithm to obtain a virtual workpiece quality.

As set forth above, in an embodiment, the disclosure acquires first detection data at an operation stage of a workpiece processing apparatus and then obtains a first virtual apparatus health index through the transform of the first and second transform models that are established chronologically, so that the disclosure may fast estimate a apparatus health index of the workpiece processing apparatus. In another embodiment, the first detection data is applied into the third transform model to obtain a second virtual apparatus health index. The comparison between the first and second virtual apparatus health indexes is used to determine whether to update the first transform model according to third detection data and relative third actual workpiece qualities. In yet another embodiment, a user may select at least one preset algorithm on an operation interface to generate a mixed algorithm related to the first transform model. Therefore, the disclosure may enhance the estimation speed and accuracy of transform models related to apparatus health indexes of an apparatus.

What is claimed is:

1. A health assessment method, performed by a health assessment apparatus and configured to assess a health state of a workpiece processing apparatus used for machining at least one workpiece, the health assessment apparatus comprising a detection data acquiring microprocessor, a first microprocessor and a second microprocessor, and the health assessment method comprising:
    acquiring a plurality of second detection data related to the workpiece processing apparatus at a previous operation stage of the workpiece processing apparatus by the detection data acquiring microprocessor;
    establishing a first transform formula in the first microprocessor according to the plurality of second detection data and a plurality of first actual workpiece qualities being in response to the plurality of second detection data, wherein the second detection data and the first actual workpiece quality are respectively assigned as an independent variable of the first transform formula and a dependent variable of the first transform formula;
    establishing a second transform formula in the second microprocessor according to a plurality of second actual workpiece qualities and a plurality of actual apparatus health index being in response to the plurality of second actual workpiece qualities, wherein the second actual workpiece quality and the actual apparatus health index are respectively assigned as an independent variable of the second transform formula and a dependent variable of the second transform formula;
    acquiring a plurality of first detection data related to the workpiece processing apparatus at an operation stage of the workpiece processing apparatus by the detection data acquiring microprocessor;
    setting the first detection data as an input of a first microprocessor to perform the first transform formula to obtain a virtual workpiece quality of the workpiece processing apparatus by the first microprocessor; and
    setting the virtual workpiece quality as an input of a second microprocessor to perform the second transform formula to obtain a first virtual apparatus health index of the workpiece processing apparatus by the second microprocessor.

2. The health assessment method according to claim 1, wherein the second transform formula is established at an off-line stage of the workpiece processing apparatus.

3. The health assessment method according to claim 1, further comprising:
    comparing the first virtual apparatus health index with a second virtual apparatus health index to determine whether to update the first transform formula; and
    updating the first transform formula according to third detection data and a plurality of relative third actual workpiece qualities when it is decided to update the first transform formula,
    wherein the third detection data is related to the workpiece processing apparatus.

4. The health assessment method according to claim 3, further comprising:
    setting the first detection data as an input of a third microprocessor to perform a third transform formula to obtain the second virtual apparatus health index.

5. The health assessment method according to claim 4, wherein comparing the first and second virtual apparatus health indexes to determine whether to update the first transform formula comprises:
    calculating an overlap ratio of probability data distribution between the first virtual apparatus health index and the second virtual apparatus health index and a performance confidence value related to the overlap ratio of probability data distribution;
    determining whether the performance confidence value is larger than a first threshold;
    when the performance confidence value is not larger than the first threshold, determining whether a forecast error of the first transform formula is larger than a second threshold; and
    when the forecast error of the first transform formula is larger than the second threshold, updating the first transform formula.

6. The health assessment method according to claim 5, wherein, after whether the forecast error of the first transform formula is larger than the second threshold is decided when the performance confidence value is not larger than the first threshold, the health assessment method further comprises:
    when the forecast error of the first transform formula is not larger than the second threshold, updating the third transform formula.

7. A health assessment apparatus applied to a workpiece processing apparatus for machining at least one workpiece, the health assessment apparatus comprising:
    a detection data acquiring microprocessor configured to acquire a plurality of first detection data related to the workpiece processing apparatus at an operation stage of the workpiece processing apparatus and a plurality of second detection data related to the workpiece processing apparatus at a previous operation stage of the workpiece processing apparatus;
    a first microprocessor coupled to the detection data acquiring microprocessor, configured to perform a first transform formula related to the plurality of second detection data and a plurality of first actual workpiece qualities being in response to the plurality of second detection data, and configured to set the first detection data as an input of the first microprocessor to perform the first transform formula to obtain a virtual workpiece quality of the workpiece processing apparatus, wherein the second detection data and the first actual workpiece quality are respectively assigned as an independent variable of the first transform formula and a dependent variable of the first transform formula; and
    a second microprocessor coupled to the first microprocessor, configured to perform a second transform formula related to a plurality of second actual workpiece qualities and a plurality of actual apparatus health index being in response to the plurality of second actual workpiece qualities, and configured to set the virtual workpiece quality as an input of the second microprocessor to perform the second transform formula to obtain a first virtual apparatus health index of the workpiece processing apparatus, wherein the second actual workpiece quality and the actual apparatus health index are respectively assigned as an independent variable of the second transform formula and a dependent variable of the second transform formula.

8. The health assessment apparatus according to claim 7, wherein the second transform formula is established at an off-line stage of the workpiece processing apparatus.

9. The health assessment apparatus according to claim 7, further comprising:
a updating determination microprocessor coupled to the first microprocessor and the second microprocessor and configured to compare the first virtual apparatus health index with a second virtual apparatus health index to determine whether to update the first transform formula, and when it is determined to update the first transform formula, to command the first microprocessor to update the first transform formula according to a third detection data and a plurality of relative third actual workpiece qualities,
wherein the third detection data is related to the workpiece processing apparatus.

10. The health assessment apparatus according to claim 9, further comprising:
a third transform microprocessor coupled to the updating determination microprocessor and configured to set the first detection data as an input of a third microprocessor to perform a third transform formula to obtain the second virtual apparatus health index.

11. The health assessment apparatus according to claim 10, wherein the updating determination microprocessor further calculates an overlap ratio of probability data distribution between the first virtual apparatus health index and the second virtual apparatus health index and a performance confidence value corresponding to the overlap ratio of probability data distribution, and determines whether the performance confidence value is larger than a first threshold; when the performance confidence value is not larger than the first threshold, the updating determination microprocessor determines whether a forecast error of the first transform formula is larger than a second threshold; and when the forecast error of the first transform formula is larger than the second threshold, the updating determination microprocessor commands the first microprocessor to update the first transform formula.

12. The health assessment apparatus according to claim 11, wherein, when the forecast error of the first transform formula is not larger than the second threshold, the updating determination microprocessor commands the third microprocessor to update the third transform formula.

13. The health assessment apparatus according to claim 7, wherein the first microprocessor further determines whether a forecast of computing time meets a system specification; and when an expected error and the forecast of computing time do not meet the system specification, the first microprocessor receives a selection command again.

* * * * *